(12) United States Patent
Sanders et al.

(10) Patent No.: US 9,404,159 B2
(45) Date of Patent: *Aug. 2, 2016

(54) TMPRSS2 FOR THE DIAGNOSIS OF PROSTATE DISEASE

(71) Applicant: Quest Diagnostics Investments Incorporated, Wilmington, DE (US)

(72) Inventors: Heather R. Sanders, Winchester, CA (US); Maher Albitar, Coto De Caza, CA (US)

(73) Assignee: QUEST DIAGNOSTICS INVESTEMENTS INCORPORATED, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,363

(22) Filed: Sep. 9, 2013

(65) Prior Publication Data

US 2014/0072972 A1    Mar. 13, 2014

Related U.S. Application Data

(62) Division of application No. 12/975,908, filed on Dec. 22, 2010, now Pat. No. 8,546,552.

(60) Provisional application No. 61/289,935, filed on Dec. 23, 2009.

(51) Int. Cl.
   *C12Q 1/68*   (2006.01)
   *C12P 19/34*  (2006.01)

(52) U.S. Cl.
   CPC ........ *C12Q 1/6886* (2013.01); *C12Q 2600/156* (2013.01); *C12Q 2600/16* (2013.01)

(58) Field of Classification Search
   None
   See application file for complete search history.

(56) References Cited

U.S. PATENT DOCUMENTS

| | | | |
|---|---|---|---|
| 5,529,925 A | 6/1996 | Morris et al. | |
| 5,695,995 A | 12/1997 | Weintraub et al. | |
| 6,444,419 B1 | 9/2002 | Wong et al. | |
| 6,451,997 B1 | 9/2002 | Morris et al. | |
| 6,902,892 B1 | 6/2005 | Salceda et al. | |
| 7,037,667 B1 | 5/2006 | Afar et al. | |
| 7,432,064 B2 | 10/2008 | Salceda et al. | |
| 7,718,369 B2 | 5/2010 | Tomlins et al. | |
| 8,426,133 B2* | 4/2013 | Sanders et al. | 435/6.12 |
| 8,815,516 B2* | 8/2014 | Sanders et al. | 435/6.12 |
| 2003/0096255 A1 | 5/2003 | Felix et al. | |
| 2003/0185830 A1 | 10/2003 | Xu et al. | |
| 2004/0259086 A1 | 12/2004 | Schlegel et al. | |
| 2005/0191673 A1 | 9/2005 | Schlegel et al. | |
| 2005/0227917 A1 | 10/2005 | Williams et al. | |
| 2006/0068425 A1 | 3/2006 | Monahan et al. | |
| 2006/0115821 A1 | 6/2006 | Einstein et al. | |
| 2007/0048738 A1 | 3/2007 | Donkena et al. | |
| 2007/0212702 A1* | 9/2007 | Tomlins et al. | 435/6 |
| 2007/0237770 A1 | 10/2007 | Lai et al. | |
| 2008/0070797 A1 | 3/2008 | Mounts | |
| 2008/0131876 A1 | 6/2008 | Hantash | |
| 2008/0260761 A1 | 10/2008 | Vartanian et al. | |
| 2008/0269157 A1 | 10/2008 | Srivastava et al. | |
| 2009/0136942 A1 | 5/2009 | Kopreski | |
| 2009/0142262 A1 | 6/2009 | Salceda et al. | |
| 2009/0170075 A1 | 7/2009 | Petrovics et al. | |
| 2009/0181378 A1 | 7/2009 | Sanders et al. | |
| 2009/0197953 A1* | 8/2009 | Heuser | A61K 31/203 514/559 |
| 2009/0208937 A1 | 8/2009 | Chinnaiyan et al. | |
| 2009/0226921 A1 | 9/2009 | Afar et al. | |
| 2009/0239221 A1 | 9/2009 | Chinnaiyan et al. | |
| 2010/0304390 A1 | 12/2010 | Sanders et al. | |

FOREIGN PATENT DOCUMENTS

| | | |
|---|---|---|
| WO | WO 2005/111235 A2 | 12/2005 |
| WO | WO-2008/063769 | 5/2008 |
| WO | WO 2008063769 A2 * | 5/2008 |
| WO | WO 2009/000912 A2 | 12/2008 |
| WO | WO-2009/102446 | 8/2009 |

OTHER PUBLICATIONS

Soverini et al., "Cyclin D1 overexpression is a favorable prognostic variable for newly diagnosed multiple myeloma patients treated with high-dose chemotherapy and single or double autologous transplantation," Blood, 2003, vol. 102, No. 5, pp. 1588-1594.*

Nasci et al., "Comparison of vero cell plaque assay, TaqMan® reverse transcriptase polymerase chain reaction RNA assay, and Vectest® antigen assay for detection of west nile virus in field-collected mosquitoes," Journal of the American Mosquito Control Association, 2002, vol. 18, No. 4, pp. 294-300.*

Hafner et al, Isothermal Amplification and Multimerization of DNA by Bst DNA Polymerase, Biotechniques, 30(4):852-860 (2001).

Han et al, Characterization of ETS gene aberrations in select histologic variants of prostate carcinoma, Mod Pathol, 22: 1176-1185 (2009).

International Search Report dated Mar. 9, 2011 in application PCT/US2010/061773.

International Search Report dated Sep. 20, 2010 in application PCT/US2009/035974.

Laxman et al, Nonivasive detection of TMPRSS2:ERG fusion transcripts in the urine of men with prostate cancer, (2006), Neoplasia, 8(10):885-888.

Lin et al. Prostate-localized and Androgen-regulated Expression of the Membrane-bound Serine Protease TMPRSS2, Cancer Research 59, 4180-4184 (1999).

Mani, et al, Induced chromosomal proximity and gene fusions in prostate cancer, Science, (2009), 326(5957):1230.

Mao et al, Detection of TMPRSS2:ERG fusion gene in circulating prostate cancer cells, (2008), Asian J Andrology, 10(3):467-473.

(Continued)

*Primary Examiner* — Young J Kim
(74) *Attorney, Agent, or Firm* — Foley & Lardner LLP

(57) ABSTRACT

Described herein are methods, compositions and kits directed to the detection the 5' portion of TMPRSS2 mRNA for the detection and diagnosis of prostate disease including prostate cancer and benign prostatic hyperplasia.

8 Claims, No Drawings

(56) References Cited

OTHER PUBLICATIONS

Nam et al, Expression of the TMPRSS2:ERG fusion gene predicts cancer recurrence after surgery for localised prostate cancer, British Journal of Cancer, (2007), 97:1690-1695.
Paoloni-Giacobino et al, Cloning of the TMPRSS2 gene, which encodes a novel serine protease with transmembrane, LDLRA, and SRCR domains and maps to 21q22.3, Genomics, 44:309-320 (1997).
Perner et al, EML4-ALK fusion lung cancer: a rare acquired event, Neoplasia, 10(3):298-302, 2008.
Pflueger et al, N-myc downstream regulated gene 1 (NDRG1) is fused to ERG in prostate cancer, Neoplasia, (2009), 11(8):804-811.
Rubin et al, Bioinformatics approach leads to the discovery of the TMPRSS2:ETS gene fusion in prostate cancer, (2006), Lab Investigation, 86:1099-1102.
Rubin et al, The basic biology of HER2, Annals of Oncology, 12(Suppl 1):S3-S8, 2001.
Shappell, Clinical utility of prostate carcinoma molecular diagnostic tests, Rev Urology, (2008), 10(1):44-69.
Tefferi et al, Chronic Myeloid Leukemia: Current Application of Cytogenetics and Molecular Testing for Diagnosis and Treatment, Mayo Clin Proc, 80(3):390-402, 2005.
Tomlins et al, Recurrent fusion of TMPRSS2 and ETS transcription factor genes in prostate cancer, Science (2005), 310(5748): 644-648.
Ueda et al, Amplification of the MYC Gene in Osteosarcoma Secondary to Paget's Disease of Bone; Sarcoma, 1(3-4):131-134, 1997.
Underwood et al, C-erbB-2 gene amplification: a molecular marker in recurrent bladder tumors?, Cancer Res., 55:2422-2430, 1995.
Vega et al. Chromosomal Translocations Involved in Non-Hodgkin Lymphomas, Arch Pathol Lab Med, 127:1148-1160, 2003.
Wharam et al, Specific detection of DNA and RNA targets using a novel isothermal nucleic acid amplification assay based on the formation of a three-way junction structure, Nucleic Acids Res, 29(11):E54-E54, (2001).
Wright et al., "Newer Potential Biomarkers in Prostate Cancer", Review in Urology 9(4):207-213 (2007).
Zhang et al., Characterization of Genomic Breakpoints in MLL and CBP in Leukemia Patients with t(II;16), Genes, Chromosomes Cancer, 41:257-65, 2004.
Zhang et al., E Protein Silencing by the Leukemogenic AML1-ETO Fusion Protein, Science, 305:1286-1289, 2004.
Office Action issued on May 18, 2012 in U.S. Appl. No. 12/786,266.
Notice of Allowance issued on Aug. 30, 2012 in U.S. Appl. No. 12/786,266.
Ar-Rushdi et al., "Differential Expression of the Translocated and the Untranslated c-*myc* Oncogene in Burkitt Lymphoma," Science, vol. 222, pp. 390-393, Oct. 28, 1983.
New England BioLabs Catalogue, 1989, pp. 121 and 284.
Soverini et al., "Cycline D1 overexpression is a favorable prognostic variable for newly diagnosed multiple myeloma patients treated with high-dose chemotherapy and single or double autologous transplantation," Blood, vol. 102, pp. 1588-1594, 2003.
Office Action issued in U.S. Appl. No. 12/975,908 on Jun. 4, 2012.
Office Action issued in U.S. Appl. No. 12/975,908 on Aug. 16, 2012.
Office Action issued in U.S. Appl. No. 12/975,908 on Nov. 28, 2012.
Office Action issued in U.S. Appl. No. 12/975,908 on Apr. 4, 2013.
Office Action issued in U.S. Appl. No. 12/975,908 on Apr. 24, 2013.
Notice of Allowance issued in U.S. Appl. No. 12/975,908 on Jun. 3, 2013.
Sanders et al., "Detection of various ALK translocations using intragenic differential expression (IDE) in patients with non-small cell lung cancer," Proceedings of the Annual Meeting of the American Association for Cancer Research, vol. 51, p. 910, Jan. 1, 2010 (Abstract).
Sanders et al., "Intragenic expression profile in tissue and plasma for the detection of TMPRSS2 rearrangements associated with prostate cancer," Journal of Clinical Oncology, vol. 27, No. 155, p. 5162, May 20, 2009 (Abstract).
Tomlins et al, "Recurrent Fusion of TMPRSS2 and ETS Transcription Factor Genes in Prostate Cancer," vol. 310, pp. 644-648, Oct. 28, 2005.
Soda et al., "Identification of the transforming EML4-ALK fusion gene in non-small-cell lung cancer," Nature, vol. 448, pp. 561-567, Aug. 2007.
Choi et al., Identification of Novel Isoforms of the EML4-ALK Transforming Gene in Non-Small Cell Lung Cancer, Cancer Research, vol. 68, pp. 4971-4976, Jul. 2008.
Supplementary European Search Report issued in application No. EP 10 78 1063 on Mar. 4, 2013.

* cited by examiner

TMPRSS2 FOR THE DIAGNOSIS OF PROSTATE DISEASE

CROSS-REFERENCE TO RELATED APPLICATIONS

This application claims benefit of U.S. Provisional Application No. 61/289,935, filed Dec. 23, 2009.

FIELD OF THE INVENTION

The present technology relates generally to detection and quantification of the 5' end of TMPRSS2 RNA from biological samples and its use for in the diagnosis and prognosis of prostate disease.

BACKGROUND OF THE INVENTION

The following description is provided to assist the understanding of the reader. None of the information provided or references cited is admitted to be prior art to the present invention.

Diseases of the prostate may be divided into three major conditions. (a) Prostatitis is an inflammation of the prostate. There are four different forms of prostatitis, each with different causes and treatments. Categories 1 (acute prostatitis) and 11 (chronic bacterial prostatitis) are uncommon, and are treated with antibiotics. Category IV is a type of leukocytosis. Category III prostatitis comprises about 95% of diagnoses, and is a chronic non-bacterial prostatitis, also known as male chronic pelvic pain syndrome. (b) Benign prostatic hyperplasia (BPH), a benign enlargement of the prostate that occurs in older men, causing urinary obstruction, increased urinary frequency, pain and discomfort. Urinary frequency due to bladder spasm, common in older men, may be confused with prostatic hyperplasia. (c) Prostate cancer is the most common cancer diagnosed in men today, with a lifetime risk of diagnosis of approximately 16%. Wright and Lange "Newer potential biomarkers in prostate cancer" *Reviews in Urology* 9(4): 207-213 (2007).

Similar diseases may also be seen in Skene's gland (also known as "female prostate" "prostate-like" or simply "prostate"), a smaller, female equivalent to the male prostate gland that also expresses PSA. This gland may also become diseased, including cancerous, resulting in elevated PSA levels.

Early detection and diagnosis of prostate cancer currently relies on digital rectal examination (DRE), prostate specific antigen (PSA) measurements, transrectal ultrasonography (TRUS), and transrectal needle biopsy (TRNB). U.S. Patent Application Publication No. 2009/0226921. Serum PSA measurements in combination with DRE represent the leading diagnostic approach at present. (Wright and Lange, Id.) PSA is prostate specific, but not prostate-cancer specific, and PSA levels are also elevated in prostatitis and BPH. The positive predictive value for cancer of a PSA>4.0 ng/mL is only 25% from a pooled metaanalysis. Lower cut-offs (e.g. 2.5 ng/mL) increase detection but decreases specificity, leading to unnecessary biopsies. Id.

A number of biomarkers have been proposed or are under investigation for detection of prostate cancer. These include PSA isoforms, human kallikreins, CpG methylation of GSTP1 and other loci (including APC, RASSF1a, RARβ2), PCA3 RNA, alpha methylacyl CoA racemase mRNA, autoantibodies, and genetic translocations. One of the most commonly tested translocations involves the ETS-related genes (ERG) at 21q22.2 and ETV1 at 7p21.2 with TMPRSS2 (21 q22.3). The fusion of these genes is seen in 40%-80% of prostate cancer patients, approximately 20% of prostatic intraepithelial neoplasia (PIN) cases, and rarely in benign prostatic tissue. Id.

TMPRSS2 is androgen regulated gene encoding "transmembrane protease, serine 2," but its function is unknown. Id. TMPRSS2 is expressed both in prostate cancer, and in normal prostate tissue. Lin et al. "Prostate-localized and Androgen-regulated Expression of the Membrane-bound Serine Protease TMPRSS2" Cancer Research 59, 4180-4184 (1999).

SUMMARY OF THE INVENTION

The present invention relates to methods, compositions, and kits for the detection and/or quantification of 5' TMPRSS2 nucleic acids (e.g., RNA) in acellular body fluids and their use in detection and diagnosis of prostate disease.

In one aspect, the invention provides a method for detecting prostate disease (e.g., prostate cancer and benign prostatic hyperplasia) in a subject by (a) amplifying a polynucleotide from a 5' region of TMPRSS2 RNA, if present, in an acellular body fluid (e.g., serum and plasma), (b) detecting the amplification product, and (c) identifying the subject has having prostate disease when the 5' region of TMPRSS2 RNA is detected. In some embodiments, the 5' region of TMRPSS2 RNA is quantified (e.g., using reverse transcriptase PCR (RT-PCR)). Optionally, the TMPRSS2 RNA is detected in real-time (e.g., using real-time RT-PCR). The 5' region of the TMPRSS2 RNA may be contained entirely within the protein coding region (e.g., following the ATG start codon of the RNA) or may contain (or be contained entirely within) the untranslated region of the TMRPSS2 RNA. Optionally, two or more discrete or overlapping 5' regions of the TMPRSS2 RNA may be assessed.

In some embodiments, the method further detects a region of an endogenous control gene RNA also present in the acellular body fluid of the subject. Suitable endogenous control genes include, for example, ABL, glyceraldehyde-3-phosphate dehydrogenase (G3PDH or GAPDH), albumin, actins, tubulins, cyclophilin, hypoxanthine phosphoribosyltransferase (HRPT), L32. 28S, and 18S rRNAs. The amount of the endogenous control gene RNA may be quantified and optionally used to normalize the amount of the 5' region of TMPRSS2 measured in the sample. Alternatively, the endogenous control gene may be used merely as a positive control to establish that RNA isolation and amplification procedures were valid and successful. Optionally, exogenous control gene nucleic acid (e.g., DNA or RNA) may be added to the sample prior to or during processing.

In other embodiments, assessment of the 5' region of TMPRSS2 RNA may be combined with other biochemical and/or clinical analyses in order to establish a diagnosis of prostate disease. For example, the TMRPSS2 result may be combined with a determination of the presence or amount of PSA in the same or a different sample obtained from the subject, or the results from a digital rectal examination (DRE), transrectal ultrasonography (TRUS), or transrectal needle biopsy (TRNB). PSA, or any other suitable biochemical marker, may be assessed by any convenient method including, for example, assessment of the marker protein or marker nucleic acid.

Detection of any 5' region of the TMPRSS2 RNA and/or endogenous control gene may be done by any suitable method including, for example, using labeled oligonucleotide probes complementary to each amplification product, or one or more detectably-labeled amplification primers.

In another aspect, the invention also provides kits useful for the diagnosis of prostate disease. Suitable kits include one or more oligonucleotides specific for a 5' region of TMPRSS2 RNA. Optionally, kits further contain one or more oligonucleotides specific for an endogenous control gene. Suitable oligonucleotides may contain one or more detectable labels and may be designed to function as primers for primer-extension reactions, or oligonucleotide detection probes.

As used herein, unless indicated otherwise, when referring to a numerical value, the term "about" means plus or minus 10% of the enumerated value.

As used herein, the term "detecting" refers to observing a signal from a detectable label to indicate the presence of a target nucleic acid in the sample. The term detecting does not require the method to provide 100% sensitivity and/or 100% specificity. As is well known, "sensitivity" is the probability that a test is positive, given that the subject has a target nucleic acid sequence, while "specificity" is the probability that a test is negative, given that the subject does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

The terms "complement," "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, for the sequence 5'-A-G-T-3' is complementary to the sequence 3'-T-C-A-5'. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Complementarity may be "partial" in which only some of the nucleic acids' bases are matched according to the base pairing rules. Or, there may be "complete," "total," or "full" complementarity between the nucleic acids.

The term "detectable label" as used herein refers to a molecule or a compound or a group of molecules or a group of compounds associated with a probe and is used to identify the probe hybridized to a genomic nucleic acid or reference nucleic acid. In some cases, the detectable label may be detected directly. In other cases, the detectable label may be a part of a binding pair, which can then be subsequently detected. Signals from the detectable label may be detected by various means and will depend on the nature of the detectable label. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

The term "endogenous control" or "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phosphoribosyltransferase (HRPT), L32. 28S, and 18S rRNAs, Abelson (ABL), beta-2-microglobulin (B2M), and beta-glucuronidase (GUS). Detection of a housekeeping gene in a diagnostic assay may serve as a positive control for the assay. In one embodiment, the control is ABL.

A "fragment" in the context of a gene fragment or a chromosome fragment refers to a sequence of nucleotide residues which are at least about 10 nucleotides, at least about 20 nucleotides, at least about 25 nucleotides, at least about 30 nucleotides, at least about 40 nucleotides, at least about 50 nucleotides, at least about 100 nucleotides, at least about 250 nucleotides, at least about 500 nucleotides, at least about 1,000 nucleotides, at least about 2,000 nucleotides.

The terms "identity" and "identical" refer to a degree of identity between sequences. There may be partial identity or complete identity. A partially identical sequence is one that is less than 100% identical to another sequence. Partially identical sequences may have an overall identity of at least 70% or at least 75%, at least 80% or at least 85%, or at least 90% or at least 95%.

As used herein, the terms "isolated," "purified" or "substantially purified" refer to molecules, such as nucleic acid, that are removed from their natural environment, isolated or separated, and are at least 60% free, preferably 75% free, and most preferably 90% free from other components with which they are naturally associated. An isolated molecule is therefore a substantially purified molecule.

The term "multiplex PCR" as used herein refers to an assay that provides for simultaneous amplification and detection of two or more products within the same reaction vessel. Each product is primed using a distinct primer pair. A multiplex reaction may further include specific probes for each product that are detectably labeled with different detectable moieties.

As used herein, the term "oligonucleotide" refers to a short polymer composed of deoxyribonucleotides, ribonucleotides, or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt, and most preferably between about 18 to about 26 nt in length.

As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the $T_m$ of the formed hybrid.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art (e.g., BLAST). As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

The term "target nucleic acid" and "target sequence" are used interchangeably herein and refer to nucleic acid sequence which is intended to be identified. Target nucleic acids may include 5' or 3' regions of a target gene or any other sequence of interest. Target nucleic acids may represent alternative sequences or alleles of a particular gene. Target nucleic acids can be double stranded or single stranded, or partially double stranded, or partially single stranded or a hairpin molecule. Target nucleic acids can be about 1-5 bases, about 10 bases, about 20 bases, about 50 bases, about 100 bases, about 500 bases, about 1,000 bases, about 2,000 bases, 2,500 bases, about 3,000 bases, or more.

"TMPRSS2" refers to the gene and its products (e.g., RNA and protein) commonly known as transmembrane protease serine 2. The mRNA sequence of several TMRPSS2 variants are known and include, for example, GenBank Accession Nos. NM_001199.1 (transcript variant 1) and NM_005656.3 (transcript variant 2) (see, for example, Han et al., Mod. Pathol. 22: 1176-1185, 2009; Paoloni-Giacobino et al., Genomics 44: 309-320, 1997).

The term "transcript," when referring to a target nucleic acid, refers to any nucleic acid transcript, including mRNA, pre-mRNA, and snRNA, and synthetic representations thereof such as cDNA.

The term "5' region" refers to the portion of a polynucleotide (e.g., a TMPRSS2 RNA) located towards the 5' end of the polynucleotide, and may or may not include the 5' most nucleotide(s) of the same polynucleotide. In the context of the present methods, the 5' region may be located near the 5' end of the transcribed portion of the TMPRSS2 gene. In some embodiments, the 5' region encompasses all or a portion of the 5' untranslated region (UTR) of the TMPRSS2 gene. In other embodiments, the 5' region includes a sequence located downstream of the start codon (if the target gene is a protein-coding gene); for example, at least 10, at least 50, at least 100, at least 200, or at least 500 nucleotides downstream of the start codon. Typically, the entire 5' region is encoded within the first 1000 nucleotide of the TMRPSS2 RNA following the start codon and optionally may include all or a portion of the UTR. Most preferably, the 5'-region being assessed is entirely 5' to a known translocation breakpoint that results in any one of the TMPRSS2 fusions. For example, TMPRSS2 translocations are known with ERG (21q22.3), ETV1 (7p21.2), and ETV4 (17q21). Thus, if the subject is suspected of having (or known to have) one of these translocations, then the 5' TMPRSS2 region under evaluation should be entirely 5' of the translocation breakpoint in the TMPRSS2 gene. The size of the 5' region to be amplified can vary depending on the detection method chosen. In some embodiments, a primer may be selected to amplify at least 10, at least 20, at least 30, at least 50, at least 100, at least 200, or at least 500 nucleotides in the 5' region.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who is, or is suspected to be, afflicted with prostate disease.

The term "prostate disease" encompasses all diseases and disorders of the prostate. These include prostatitis, benign prostatic hyperplasia (BPH), and prostate cancer. Ordinarily, this would be of most interest to males, but also includes diseases of Skene's gland in females.

As used herein, the phrase "difference of the level" of TMPRSS2 expression refers to differences in the quantity of transcript from the 5' region of a gene over the amount of transcript normally detected, normalized to the level of expression of a given control, such as a housekeeping gene. Methods for comparing the difference of the level are known to those of skill in the art and include, but are not limited to, a Student's t-test and ANOVA analysis.

DETAILED DESCRIPTION

The present invention provides methods for detecting 5' TMPRSS2 RNA (e.g., mRNA) expression in acellular fluids, including e.g., plasma and serum. This disclosure is also drawn, inter alia, to methods of diagnosing or monitoring prostate cancer, and distinguishing prostate cancer from other prostate diseases including, for example, BPH.

In some embodiments, a sample obtained from a subject is assayed to determine the expression levels of the 5' region of TMPRSS2. RT-PCR (reverse transcription-polymerase chain reaction) is a sensitive technique for mRNA detection and quantitation. Amplification and detection using RT-PCR may be performed in a real-time format such as TaqMan®. Compared to the two other commonly used techniques for quantifying mRNA levels, Northern blot analysis and RNase protection assays, RT-PCR can be used to quantify mRNA levels from much smaller samples. In fact, this technique is sensitive enough to enable quantitation of RNA from a single cell.

One of skill in the art would know how to design oligonucleotide primers and probes that are used to detect the presence of 5'TMPRSS2 RNA (e.g., mRNA) in a sample.

Certain primers, however, may be advantageous over other primers to the same general region in terms of binding or amplification specificity and sensitivity or other factors that are relevant to the compositions and methods of the invention. The size of the primer will depend on many factors, including the ultimate function or use of the oligonucleotide. An oligonucleotide that functions as an extension primer or probe, for example, will be sufficiently long to prime the synthesis of extension products in the presence of a catalyst, e.g., DNA polymerase, and deoxyribonucleotide triphosphates.

Target Nucleic Acids and Primers.

The methods of the present invention relate to the detection of TMPRSS2 by amplifying a 5' region of TMPRSS mRNA, if present, in a biological sample with one or more 5' target primer pairs which are complementary to the 5' region of the target gene. Such regions can be amplified and isolated by PCR using oligonucleotide primers designed based on mRNA and/or cDNA sequences that encompass the regions.

Sample Preparation.

Specimens from which target nucleic acids can be detected and quantified with the methods of the present invention may be obtained from subjects according to methods known to those of skill in the art.

The nucleic acid (DNA and/or RNA) may be isolated from the sample according to any methods well known to those of skill in the art. If necessary, the sample may be collected or concentrated by centrifugation and the like. The cells of the sample may be subjected to lysis, such as by treatments with enzymes, heat surfactants, ultrasonication or combinations thereof. The lysis treatment is performed in order to obtain a sufficient amount of RNA derived from the cells of interest, if present in the sample, to detect using RT-PCR. Nucleic acid need not be extracted, but may be made available by suitable treatment of cells or tissue such as described in US Patent Publication No. 2008/131876.

In one embodiment, mRNA or cDNA generated from mRNA or total RNA may be used. Various methods of RNA extraction are suitable for isolating the RNA. Suitable methods include phenol and chloroform extraction. See Maniatis et al., *Molecular Cloning, A Laboratory Manual*, 2d, Cold Spring Harbor Laboratory Press, page 16.54 (1989). In addition kits for isolating mRNA and synthesizing cDNA are commercially available e.g., RNeasy Protect Mini kit, RNeasy Protect Cell Mini kit from Qiagen.

In one embodiment, a dual RNA/DNA isolation method is used employing a trizol based reagent for initial isolation of RNA and DNA from patient samples. Upon contact with patient samples, the phenol and high salt reagents in the trizol effectively inactivate any disease agent or secondary disease agent that may be present in the patient sample. After the RNA and DNA are isolated from the patient samples, a silica based column may be used to further isolate the RNA and DNA. The use of silica based columns allows for wash steps to be performed quickly and efficiently while minimizing the possibility of contamination. The wash steps may be used to remove PCR and RT-PCR inhibitors. The column method for nucleic acid purification is advantageous as it can be used with different types of patient samples and the spin and wash steps effectively remove PCR or RT-PCR inhibitors. In another embodiment, the RNA and/or DNA may be isolated from the sample (e.g., an acellular body fluid sample) using the NucliSENS® DNA/RNA extraction kit (Biomerieux SA, France) according to the manufacturer's protocol. Optionally, following isolation, the RNA may be concentrated prior to further processing. Any suitable method for RNA concentration may be used including, for example, the Qiagen RNeasy® Micro kit, according to manufacturer's protocol.

Preparation of cDNA.

Most conveniently, the RNA isolated from the samples is first converted into cDNA. The production of cDNA may be done by any appropriate method. Some methods employ reverse transcription of RNA to cDNA. As noted, the method of reverse transcription and amplification may be performed by previously published or recommended procedures, which referenced publications are incorporated herein by reference in their entirety. Various reverse transcriptases may be used, including, but not limited to, MMLV RT, RNase H mutants of MMLV RT such as Superscript™, Superscript II™, and Superscript III™ (Life Technologies, GIBCO BRL, Gaithersburg, Md.), AMV RT, and thermostable reverse transcriptase from *Thermus Thermophilus*. For example, one method, but not the only method, which may be used to convert RNA extracted from plasma or serum to cDNA is the protocol adapted from the Superscript II Preamplification system (Life Technologies, GIBCO BRL, Gaithersburg, Md.; catalog no. 18089-011), as described by Rashtchian, A., *PCR Methods Applic.*, 4:S83-S91, (1994).

Amplification of Nucleic Acids.

Nucleic acid samples or target nucleic acids may be amplified by various methods known to the skilled artisan. In suitable embodiments, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

In one embodiment, the target nucleic acids are amplified in a multiplex amplification reaction. A variety of multiplex amplification strategies are known in the art and may be used with the methods of the invention. The multiplex amplification strategy may use PCR, RT-PCR or a combination thereof depending on the type of nucleic acid contained in the disease agent(s). For example, if an RNA genome is present, RT-PCR may be utilized. The PCR enzyme may be an enzyme with both a reverse transcription and polymerase function. Furthermore, the PCR enzyme may be capable of "hot start" reactions as is known in the art.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended. An internal positive amplification control (IC) can be included in the sample, utilizing oligonucleotide primers and/or probes.

In one embodiment, the synthesis of cDNA from RNA by reverse transcription and cDNA amplification may be performed in a single assay. For example, the Superscript® III One-step RT-PCR system (Invitrogen, Carlsbad, Calif.) utilizes the simultaneous combination of a reverse transcriptase (Superscript®) and a DNA polymerase (Taq polymerase) to achieve both reverse transcription and amplification in a single step.

Detection of Amplified Nucleic Acids.

Amplification of nucleic acids can be detected by methods known in the art such as gel electrophoresis, column chromatography, hybridization with a probe, sequencing, melting curve analysis, or "real-time" detection.

In one approach, sequences from two or more fragments of interest are amplified in the same reaction vessel (i.e., "multiplex PCR"). Detection can take place by measuring the end-point of the reaction or in "real time." For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, the Scorpion™ bi-functional molecule, and the use of intercalating dyes for double stranded nucleic acid.

In end-point detection, the amplicon(s) can be detected by first size-separating the amplicons, then detecting the size-separated amplicons. The separation of amplicons of different sizes can be accomplished by, e.g., gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 10% polyacrylamide gel. The separated nucleic acids can then be stained with a dye such as ethidium bromide and the size of the resulting stained band or bands can be compared to a standard DNA ladder.

In another embodiment, two or more fragments of interest are amplified in separate reaction vessels. If the amplification is specific, that is, one primer pair amplifies for one fragment of interest but not the other, detection of amplification is sufficient to distinguish between the two types—size separation would not be required.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). In some embodiments, the amplified DNA is detected simultaneously, using two or more distinguishably-labeled, gene-specific oligonucleotide probes, one which hybridizes to the first target sequence and one which hybridizes to the second target sequence.

The probe may be detectably labeled by methods known in the art. Useful labels include, e.g., fluorescent dyes (e.g., Cy5®, Cy3®, FITC, rhodamine, lanthamide phosphors, Texas red, FAM, JOE, Cal Fluor Red 610®, Quasar 670®), $^{32}P$, $^{35}S$, $^{3}H$, $^{14}C$, $^{125}I$, $^{131}I$, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) that hybridizes or binds to the nucleic acid to be detected.

One general method for real time PCR uses fluorescent probes such as the TaqMan® probes, molecular beacons, and Scorpions™. Real-time PCR quantitates the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

In one embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from decreased distance between the donor and the quencher (acceptor fluorophore).

Suitable fluorescent moieties include the following fluorophores known in the art: 4-acetamido-4'-isothiocyanatostilbene-2,2' disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Black Hole Quencher (BHQ™) dyes (Biosearch Technologies), BODIPY® R-6G, BOPIPY® 530/550, BODIPY® FL, Brilliant Yellow, coumarin and derivatives (coumarin, 7-amino-4-methylcoumarin (AMC, Coumarin 120), 7-amino-4-trifluoromethylcouluarin (Coumarin 151)), Cy2®, Cy3®, Cy3.5®, Cy5®, Cy5.5®, cyanosine, 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET)), fluorescamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tetramethyl-6-carboxyrhodamine (TAMRA), tetramethyl rhodamine, tetramethyl rhodamine isothiocyanate (TRITC), CAL Fluor Red 610, Quasar 670, riboflavin, rosolic acid, terbium chelate derivatives.

Other fluorescent nucleotide analogs can be used, see, e.g., Jameson, 278 *Meth. Enzymol.*, 363-390 (1997); Zhu, 22 *Nucl. Acids Res.*, 3418-3422 (1994). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, *Mol. Cell. Probes,* 9:145-156 (1995). Detectable labels may be incorporated into nucleic acids by covalent or non-covalent means, e.g., by transcription, such as by random-primer labeling using Klenow polymerase, or nick translation, or amplification, or equivalents known in the art. For example, a nucleotide base is conjugated to a detectable moiety, such as a fluorescent dye, and then incorporated into nucleic acids during nucleic acid synthesis or amplification.

With Scorpion™ probes, sequence-specific priming and PCR product detection is achieved using a single molecule. The Scorpion™ probe maintains a stem-loop configuration in the unhybridized state. The fluorophore is attached to the 5' end and is quenched by a moiety coupled to the 3' end The 3' portion of the stem also contains sequence that is complementary to the extension product of the primer. This sequence is linked to the 5' end of a specific primer via a non-amplifiable monomer. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™, resulting in an extension product. A fluorescent signal is generated due to the separation of the fluorophore from the quencher resulting from the binding of the probe element of the Scorpion™ to the extension product.

TaqMan® probes (Heid et al., *Genome Res,* 6:986-994, 1996) use the fluorogenic 5' exonuclease activity of Tag polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi et al., *Nature Biotechnology,* 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In a suitable embodiment, real-time PCR is performed using any suitable instrument capable of detecting fluorescence from one or more fluorescent labels. For example, real time detection on the instrument (e.g., a ABI Prism® 7900HT sequence detector) monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually. The Ct value may be correlated to the amount of initial template nucleic acid in the reaction.

In some embodiments, melting curve analysis may be used to detect an amplification product. Melting curve analysis involves determining the melting temperature of nucleic acid amplicon by exposing the amplicon to a temperature gradient and observing a detectable signal from a fluorophore. Melting curve analysis is based on the fact that a nucleic acid sequence melts at a characteristic temperature called the melting temperature ($T_m$), which is defined as the temperature at which half of the DNA duplexes have separated into single strands. The melting temperature of a DNA depends primarily upon its nucleotide composition. Thus, DNA molecules rich in G and C nucleotides have a higher $T_m$ than those having an abundance of A and T nucleotides.

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. In some embodiments, the fluorescent dye for determining the melting temperature of a nucleic acid may be excited by different wavelength energy than any other of the different fluorescent dyes that are used to label the oligonucleotides. In some embodiments, the second fluorescent dye for determining the melting temperature of the detected nucleic acid is an intercalating agent. Suitable intercalating agents may include, but are not limited to SYBR™ Green 1 dye, SYBR™ dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ Green 1 dye.

By detecting the temperature at which the fluorescence signal is lost, the melting temperature can be determined. In the disclosed methods, each of the amplified target nucleic acids may have different melting temperatures. For example, each of these amplified target nucleic acids may have a melting temperature that differs by at least about 1° C., more preferably by at least about 2° C., or even more preferably by at least about 4° C. from the melting temperature of any of the other amplified target nucleic acids.

Methods of Diagnosis.

In one aspect, the methods described herein provide for diagnosing prostate disease, prostate cancer or a susceptibility to prostate cancer in a subject. The term "diagnose" or "diagnosis" as used herein refers to the act or process of identifying or determining a disease or condition in an organism or the cause of a disease or condition by the evaluation of the signs and symptoms of the disease or disorder. Usually, a diagnosis of a disease or disorder is based on the evaluation of one or more factors and/or symptoms that are indicative of the disease. That is, a diagnosis can be made based on the presence, absence, or amount, of a factor which is indicative of presence or absence of the disease or condition. Each factor or symptom that is considered to be indicative for the diagnosis of a particular disease does not need be exclusively related to the particular disease, i.e., there may be differential diagnoses that can be inferred from a diagnostic factor or symptom. Likewise, there may be instances where a factor or symptom that is indicative of a particular disease is present in an individual that does not have the particular disease.

Methods of Prognosis.

In one aspect, the methods described herein provide a prognosis for prostate cancer or in a subject. The term "prognosis" as used herein refers to a prediction of the probable course and outcome of a clinical condition or disease. A prognosis of a patient is usually made by evaluating factors or symptoms of a disease that are indicative of a favorable or unfavorable course or outcome of the disease. The term prognosis does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

A prognosis is often determined by examining one or more prognostic factors or indicators. These are markers, such as the presence of a particular chromosomal translocation, the presence or amount of which in a patient (or a sample obtained from the patient) signal a probability that a given course or outcome will occur. The skilled artisan will understand that associating a prognostic indicator with a predisposition to an adverse outcome may involve statistical analysis.

EXAMPLES

Example 1

TMPRSS2 Detection in Plasma

TMPRSS2 is expressed mainly in the prostate. This experiment demonstrates that 5' TMPRSS2 expression (RNA) can be detected in the peripheral blood, specifically plasma, of prostate cancer patients more frequently and at a higher level than in healthy subjects. A total of 116 plasma samples (26 normal, 27 BPH, and 63 Prostate cancer) were collected over a period of approximately 2 years from multiple sources. RNA was extracted from each plasma specimen and the presence of 5'-portion and 3'-portion of TMPRSS2 RNA, as well as ABL RNA as an endogenous control, was evaluated. Detection of ABL was used as a quality control (QC) measurement to determine if the quality and quantity of RNA was sufficient for optimal assay performance (ABL Ct<40).

Difference were observed in assay performance observed depending on the source of plasma samples. The source indicates groups of samples that were drawn at different times and locations. As shown in Table 1, the nucleic acid quality varied by the source of the plasma samples and not every sample contained sufficient nucleic acid to meet the threshold criteria (ABL Ct<40) for clinical assessment using TMPRSS2.

TABLE 1

Assessment of RNA Quality Grouped by Specimen Source

| Source | Passed QC (ABL < 40) |
|---|---|
| Source #1 | 92% (24/26) |
| Source #2 | 89% (8/9) |
| Source #3 | 80% (12/15) |
| Source #4 | 61% (34/56) |
| Source #5 | 60% (6/10) |
| Total | 72% (84/116) |

Detection of TMPRSS2

The presence in the plasma samples of a 5' region and a 3'-region of TMPRSS2 was assessed in those plasma samples that were found to have sufficient quantity and quality of nucleic acids (ABL Ct<40). Overall analysis of assay results demonstrate that the 5' region of TMPRSS2 can be detected in >25% of donors with prostate cancer and approximately 5% from donors without prostate cancer (12% with BPH and 0% with no prostate condition as shown in Table 2).

TABLE 2

Results of TMPRSS2 Analysis in Plasma Samples

| Diagnosis | Passed QC ABL (Ct < 40) | 5' Positive (Ct < 40) | 3' Positive (Ct < 35) |
|---|---|---|---|
| Non-cancer | 77% (41/53) | 4.9% (2/41) | 7.3% (3/41) |
| Normal | 92% (24/26) | 0% (0/24) | 0% (0/24) |
| BPH | 63% (17/27) | 12% (2/17) | 17.6% (3/17) |
| Prostate Cancer | 68% (43/63) | 26% (11/43) | 9% (4/43) |

To address the variation observed between plasma samples obtained from different sources, detection rates are broken down by source in Table 3. The detection rates show a similar trend to assay performance with about 40% of prostate cancer samples yielding positive results from 2 sources and less than 20% positivity from 2 other sources.

TABLE 3

TMRPSS2 Results Categorized by Sample Source

| Source | Passed QC ABL (Ct < 40) | 5' Positive (Ct < 40) | 3' Positive (Ct < 35) |
|---|---|---|---|
| BPH | | | |
| Source #4 | 68% (17/25) | 12% (2/17) | 18% (3/17) |
| Source #5 | 0% (0/2) | 0% (0/2) | 0% (0/2) |
| Prostate Cancer | | | |
| Source #2 | 89% (8/9) | 38% (3/8) | 0% (0/8) |
| Source #3 | 80% (12/15) | 42% (5/12) | 0% (0/12) |
| Source #4 | 55% (17/31) | 18% (3/17) | 18% (3/17) |
| Source #5 | 75% (6/8) | 13% (1/8) | 0% (0/8) |

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Other embodiments are set forth within the following claims.

What is claimed is:

1. A method for determining whether a TMPRSS2 RNA is present in an acellular body fluid, comprising:
   (a) performing real-time reverse transcription polymerase chain reaction (RT PCR) on an acellular body fluid sample to amplify a polynucleotide from a 5' region of TMPRSS2 RNA, if present, and a polynucleotide from a region of an endogenous control gene RNA present in the acellular body fluid, thereby generating a 5' TMPRSS2 amplification product, if the TMPRSS2 RNA is present, and an amplification product generated from the endogenous control gene;
   (b) determining the Ct value of the 5' TMPRSS2 amplification product, if any, and the control gene amplification product;
   (c) identifying the TMPRSS2 RNA as present if both the 5' TMPRSS2 amplification product and the control gene amplification product have a Ct value of less than 40;
   wherein amplification of the 5' TMPRSS2 RNA is carried out with at least one primer pair comprising a forward primer and a reverse primer that bind to the 5' region of TMPRSS2;
   wherein the 5' region of TMPRSS2 that is amplified is contained entirely within or overlaps with the 5' untranslated region of the TMPRSS2 RNA; and
   wherein the endogenous control gene is ABL.

2. The method of claim 1, wherein the amplification of the 5' TMPRSS2 RNA and the control gene RNA are performed in the same reaction vessel.

3. The method of claim 1, wherein at least one of the primers in the at least one primer pair comprises a detectable label.

4. The method of claim 1, wherein the 5' TMPRSS2 amplification product, if any, is detected using an oligonucleotide probe comprising a detectable label.

5. The method of claim 1, further comprising assessing the amount of prostate-specific antigen (PSA) in the acellular body fluid.

6. The method of claim 1, wherein the acellular body fluid is serum or plasma.

7. The method of claim 1, wherein two or more regions of the 5' region of the TMPRSS2 RNA are amplified.

8. The method of claim 7, wherein the amplification products of the two or more regions of the 5' region of the TMPRSS2 RNA overlap.

\* \* \* \* \*